United States Patent
Kopp et al.

(10) Patent No.: US 11,951,273 B2
(45) Date of Patent: Apr. 9, 2024

(54) COUPLING SYSTEM FOR A CLOSED FLUID TRANSFER SYSTEM

(71) Applicant: B. Braun Melsungen AG, Melsungen (DE)

(72) Inventors: Florin Kopp, Schortens (DE); Karl Martin Berg, Melsungen (DE); Konstantin Krug-Sauer, Gudensberg (DE); Johannes Bolz, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 17/908,012

(22) PCT Filed: Mar. 3, 2021

(86) PCT No.: PCT/EP2021/055260
§ 371 (c)(1),
(2) Date: Aug. 30, 2022

(87) PCT Pub. No.: WO2021/175890
PCT Pub. Date: Sep. 10, 2021

(65) Prior Publication Data
US 2023/0090634 A1  Mar. 23, 2023

(30) Foreign Application Priority Data
Mar. 6, 2020  (DE) ............ 10 2020 202 939.3

(51) Int. Cl.
*A61M 39/10* (2006.01)
*F16L 37/46* (2006.01)

(52) U.S. Cl.
CPC .......... *A61M 39/10* (2013.01); *F16L 37/46* (2013.01); *F16L 2201/44* (2013.01)

(58) Field of Classification Search
CPC .......... A61M 39/10; A61M 2039/1027; A61M 2039/1066; A61M 2039/1072; A61M 39/26; A61M 2039/1033
See application file for complete search history.

(56) References Cited

U.S. PATENT DOCUMENTS 5,061,264 A    10/1991  Scarrow
5,122,123 A *  6/1992  Vaillancourt ......... A61M 39/14
                                                          604/905

(Continued)

FOREIGN PATENT DOCUMENTS

AU    2013200393 B2    5/2014
AU    2014277764 A1    1/2015

(Continued)

OTHER PUBLICATIONS

Search Report received in German Application No. 10 2020 202 939.3 dated Nov. 23, 2020, with translation, 14 pages.

(Continued)

*Primary Examiner* — David Colon-Morales
(74) *Attorney, Agent, or Firm* — Christopher A. Rothe; Culhane Meadows PLLC

(57) ABSTRACT

A coupling system for a closed fluid transfer system includes a coupling member that features a coupling member housing. The coupling member housing includes a housing portion that at least partially surrounds a sealing member receptacle in an axial direction with respect to the longitudinal axis and which includes a coupling member housing threaded portion on the inner surface facing the sealing member. The coupling system also includes a mating coupling member for coupling with the coupling member. The mating coupling member includes a mating coupling member housing that has a mating coupling member guiding structure. The coupling member housing threaded portion of the coupling member is configured such that the mating (Continued)

coupling member guiding structure and the sealing member receptacle structure are jointly and movably guided, in particular in a predetermined positional relation to each other, by the coupling member housing threaded portion.

16 Claims, 9 Drawing Sheets

(56) References Cited

U.S. PATENT DOCUMENTS

| | | | |
|---|---|---|---|
| 5,201,717 A | | 4/1993 | Wyatt et al. |
| 5,514,117 A | * | 5/1996 | Lynn .................... A61M 5/3213 |
| | | | 604/536 |
| 7,004,934 B2 | | 2/2006 | Vaillancourt |
| 7,080,672 B2 | | 7/2006 | Fournie et al. |
| 7,137,654 B2 | | 11/2006 | Segal et al. |
| 7,396,051 B2 | | 7/2008 | Baldwin et al. |
| 7,497,848 B2 | | 3/2009 | Einsing et al. |
| 7,628,781 B2 | | 12/2009 | Roy et al. |
| 8,196,614 B2 | | 6/2012 | Kriheli |
| 8,262,641 B2 | | 9/2012 | Vedrine et al. |
| 8,267,127 B2 | | 9/2012 | Kriheli |
| 8,287,513 B2 | | 10/2012 | Ellstrom et al. |
| 8,870,832 B2 | | 10/2014 | Raday et al. |
| 8,915,902 B2 | | 12/2014 | Reynolds et al. |
| 8,926,583 B2 | | 1/2015 | Ellstrom et al. |
| 9,039,047 B2 | | 5/2015 | Imai |
| 9,345,643 B2 | | 5/2016 | Okiyama |
| 9,370,466 B2 | | 6/2016 | Garfield et al. |
| 9,493,281 B2 | | 11/2016 | Ohlin et al. |
| 9,510,997 B2 | | 12/2016 | Kriheli et al. |
| 9,541,227 B2 | | 1/2017 | Okiyama |
| 9,549,873 B2 | | 1/2017 | Barrelle et al. |
| 9,579,258 B2 | | 2/2017 | Fukuoka |
| 9,636,278 B2 | * | 5/2017 | Sanders ................ A61J 1/1406 |
| 9,642,775 B2 | | 5/2017 | Sanders et al. |
| 9,724,504 B2 | | 8/2017 | Fangrow, Jr. et al. |
| 9,775,979 B2 | | 10/2017 | Okiyama |
| 9,820,913 B2 | | 11/2017 | Genosar |
| 9,855,192 B2 | | 1/2018 | Kim et al. |
| 9,877,895 B2 | | 1/2018 | Garfield et al. |
| 9,933,094 B2 | * | 4/2018 | Fangrow ............... A61M 39/26 |
| 9,951,899 B2 | | 4/2018 | Py et al. |
| 9,974,939 B2 | | 5/2018 | Fangrow, Jr. |
| 9,987,477 B2 | | 6/2018 | Winsor |
| 9,993,636 B2 | | 6/2018 | Uber, III et al. |
| 9,999,569 B2 | | 6/2018 | Kriheli |
| 10,022,301 B2 | | 7/2018 | Ivosevic et al. |
| 10,022,492 B2 | * | 7/2018 | Yang .................... A61M 39/26 |
| 10,022,531 B2 | * | 7/2018 | Shemesh ............ A61M 39/1011 |
| 10,058,693 B2 | | 8/2018 | Phillips et al. |
| 10,137,237 B2 | | 11/2018 | Bengtsson et al. |
| 10,156,306 B2 | | 12/2018 | Fangrow |
| 10,206,853 B2 | | 2/2019 | Sanders et al. |
| 10,206,854 B2 | | 2/2019 | Wu et al. |
| 10,335,536 B2 | | 7/2019 | Melander et al. |
| 10,357,430 B2 | | 7/2019 | Kriheli et al. |
| 10,376,654 B2 | * | 8/2019 | Sanders ................ A61J 1/2096 |
| 10,398,627 B2 | * | 9/2019 | Kriheli .................... A61J 1/201 |
| 10,441,507 B2 | | 10/2019 | Sanders |
| 10,456,329 B2 | * | 10/2019 | Sanders ................ A61J 1/2048 |
| 10,470,974 B2 | | 11/2019 | Sanders et al. |
| 10,518,078 B2 | | 12/2019 | Bejhed et al. |
| 10,561,802 B2 | * | 2/2020 | Kim ...................... A61M 5/347 |
| 10,632,044 B2 | | 4/2020 | Garfield et al. |
| 10,682,505 B2 | | 6/2020 | Shemesh |
| 10,894,317 B2 | | 1/2021 | Garfield et al. |
| 10,945,922 B1 | | 3/2021 | Cairns |
| 2008/0097371 A1 | | 4/2008 | Shemesh |
| 2009/0035383 A1 | | 2/2009 | Ohta et al. |
| 2009/0069783 A1 | | 3/2009 | Ellstrom et al. |
| 2009/0299295 A1 | | 12/2009 | Rubinstein et al. |
| 2011/0282298 A1 | | 11/2011 | Agian et al. |
| 2012/0316536 A1 | | 12/2012 | Carrez et al. |
| 2013/0006211 A1 | | 1/2013 | Takemoto |
| 2013/0072893 A1 | | 3/2013 | Takemoto |
| 2013/0076019 A1 | | 3/2013 | Takemoto |
| 2013/0144246 A1 | * | 6/2013 | Takemoto .......... A61M 39/1011 |
| | | | 604/403 |
| 2013/0296791 A1 | | 11/2013 | Segev et al. |
| 2014/0263322 A1 | | 9/2014 | Ghodbane et al. |
| 2015/0123398 A1 | | 5/2015 | Sanders et al. |
| 2015/0126958 A1 | | 5/2015 | Sanders et al. |
| 2015/0126974 A1 | | 5/2015 | Sanders et al. |
| 2016/0008544 A1 | | 1/2016 | Molson et al. |
| 2017/0209682 A1 | | 7/2017 | Shemesh |
| 2018/0000690 A1 | | 1/2018 | Eichelkraut et al. |
| 2018/0028402 A1 | | 2/2018 | Kriheli et al. |
| 2018/0161245 A1 | | 6/2018 | Kriheli |
| 2018/0200147 A1 | | 7/2018 | Sanders |
| 2018/0200148 A1 | | 7/2018 | Sanders |
| 2018/0200498 A1 | | 7/2018 | Sanders |
| 2019/0000718 A1 | | 1/2019 | Kriheli et al. |
| 2019/0046410 A1 | | 2/2019 | Shemesh |
| 2019/0053980 A1 | | 2/2019 | West et al. |
| 2019/0060171 A1 | | 2/2019 | Lee |
| 2019/0184152 A1 | | 6/2019 | Kakinoki |
| 2019/0290543 A1 | | 9/2019 | McKinnon et al. |
| 2019/0321261 A1 | | 10/2019 | Oshinski et al. |
| 2020/0323734 A1 | | 10/2020 | Ueda et al. |
| 2022/0260189 A1 | | 8/2022 | Deuse |

FOREIGN PATENT DOCUMENTS

| | | | | |
|---|---|---|---|---|
| DE | 102019116970 A1 | | 12/2020 | |
| EP | 2298407 A1 | * | 3/2011 | ............ A61J 1/2096 |
| EP | 2589368 A1 | | 5/2013 | |
| EP | 3067037 A1 | | 9/2016 | |
| EP | 3517164 A1 | | 7/2019 | |
| EP | 3607993 A1 | | 2/2020 | |
| IL | 214990 A | | 6/2013 | |
| IL | 257415 B | | 1/2020 | |
| IL | 257417 B | | 11/2020 | |
| WO | 2008129550 A2 | | 10/2008 | |
| WO | 2009035383 A1 | | 3/2009 | |
| WO | 2011150037 A1 | | 12/2011 | |
| WO | 2012117648 A1 | | 9/2012 | |
| WO | 2013036854 A1 | | 3/2013 | |
| WO | 2014122643 A1 | | 8/2014 | |
| WO | 2014181320 A1 | | 11/2014 | |
| WO | 2015017858 A1 | | 2/2015 | |
| WO | 2015069643 A1 | | 5/2015 | |
| WO | 2016042544 A1 | | 3/2016 | |
| WO | 2016199133 A1 | | 12/2016 | |
| WO | 2017066406 A1 | | 4/2017 | |
| WO | 2017109776 A1 | | 6/2017 | |
| WO | 2017183031 A1 | | 10/2017 | |
| WO | 2018174265 A1 | | 9/2018 | |
| WO | 2019033004 A1 | | 2/2019 | |
| WO | 2019086589 A1 | | 5/2019 | |
| WO | 2019135219 A2 | | 7/2019 | |
| WO | 2019167035 A1 | | 9/2019 | |
| WO | 2019187838 A1 | | 10/2019 | |
| WO | 2019187839 A1 | | 10/2019 | |
| WO | 2020031174 A1 | | 2/2020 | |
| WO | 2021019532 A1 | | 2/2021 | |

OTHER PUBLICATIONS

Search Report received in International Application No. PCT/EP2021/055260 dated May 31, 2021, with translation, 5 pages.
Written Opinion received in International Application No. PCT/EP2021/055260 dated May 31, 2021, with translation, 22 pages.

* cited by examiner

COUPLING SYSTEM FOR A CLOSED FLUID TRANSFER SYSTEM

CROSS-REFERENCE TO RELATED APPLICATIONS

This application is the United States national stage entry of International Application No. PCT/EP2021/055260, filed Mar. 3, 2021, and claims priority to German Application No. 10 2020 202 939.3, filed Mar. 6, 2020. The contents of International Application No. PCT/EP2021/055260 and German Application No. 10 2020 202 939.3 are incorporated by reference herein in their entireties.

FIELD

The invention relates to a coupling system for a closed fluid transfer system.

BACKGROUND

Many substances that are administered as injections or in a comparable form of delivery, such as CMR drugs, which are used in cancer therapy, for example, and whose therapeutic application is primarily aimed at damaging growth-intensive tumor cells, have a considerable hazard potential outside the actual therapeutic application. Due to their mechanism of action, some of these substances are themselves carcinogenic, which is why contact with persons not undergoing therapy must be avoided. Closed system transfer devices (CSTDs) are therefore increasingly being used for CMR drugs in the manufacture of ready-to-use preparations. An important component of such CSTDs are coupling systems that enable the safe transfer of CMR drugs or other substances and dry seal after disconnection, thus protecting the environment from contamination, e.g. through leakage or droplet formation on the surfaces of the coupling members.

Coupling systems of this type are, in general, associated with the terms "dry connection", "automatic self-sealing technology" or "closed connection" and are essential for the realization of closed fluid transfer systems.

Known coupling systems are often complex with respect to their handling and connection structures and may provide poor flow rates. Furthermore, fluid residues may occur on the sealing surfaces and coupling surfaces, respectively, if a constant surface pressure of the sealing surfaces is not maintained.

All current systems have in common, that they are comparably large, which results in disadvantages during an application near a patient, and that at least a coupling member or a mating coupling member provides poor accessibility of the coupling and mating coupling surface, respectively, due to their structure so that disinfection is hampered.

SUMMARY

In view of the disadvantages associated with the prior art, it is the object of the present invention to provide a coupling member, a mating coupling member and a coupling system for a closed fluid transfer system, in which the respective coupling surfaces are dry-locked in the disconnected state and are capable of being handled safely in a simple manner.

The inventive object is solved by a coupling system for a closed fluid transfer system, which comprises:

at least one coupling member for a closed fluid transfer system, comprising:

a coupling member housing, wherein the coupling member housing comprises a housing portion, which at least partially surrounds a sealing member receptacle in an axial direction with respect to the longitudinal axis and which comprises a coupling member housing threaded portion on the inner surface facing the sealing member, and a mating coupling member for coupling with the coupling member, comprising:

a mating coupling member housing, wherein the mating coupling member housing comprises a mating coupling member guiding structure;

wherein the coupling member housing threaded portion of the coupling member is configured such that the mating coupling member guiding structure and the sealing member receptacle structure are jointly movable guided, in particular in a predetermined positional relation to each other, by the coupling member housing threaded portion.

According to the invention, the coupling system for a closed fluid transfer system comprises at least one coupling member for a closed fluid transfer system and at least one mating coupling member for a closed fluid transfer system. The coupling member for a closed fluid transfer system comprises a coupling member housing comprising a fluid connection and a coupling side, wherein the coupling member housing provides a longitudinal axis extending from the fluid connection toward the coupling side, a spike with at least one fluid opening, which is held in a spike receptacle of the housing arranged at the fluid connection and extends into the coupling member housing in the direction of the longitudinal axis, wherein the at least one fluid opening is arranged in an end portion of the spike facing the coupling side, a sealing member receptacle arranged in the coupling member housing on the coupling side, a sealing member arranged in the sealing member receptacle, wherein the coupling member housing comprises a housing portion, which at least partially surrounds the sealing member receptacle in an axial direction with respect to the longitudinal axis and comprises a coupling member housing threaded portion on the inner surface facing the sealing member, wherein the sealing member receptacle with the sealing member is moveable in the direction of the longitudinal axis between a sealing member receptacle position with maximum distance to the fluid connection and a sealing member receptacle position with minimum distance to the fluid connection, and wherein the coupling member housing threaded portion is configured such that a sealing member receptacle guiding structure of the sealing member receptacle is movable in engagement with the coupling member housing threaded portion between the sealing member receptacle position with maximum distance to the fluid connection and the sealing member receptacle position with minimum distance to the fluid connection, wherein the coupling member housing threaded portion provides a height or length, respectively, of the thread in the direction of the longitudinal axis between the sealing member receptacle position with maximum distance to the fluid connection and the sealing member receptacle position with minimum distance to the fluid connection, which is more than the height or length, respectively, of the sealing member receptacle guiding structure in this direction.

Due to the interaction of the sealing member receptacle guiding structure with the coupling member housing threaded portion, the sealing member receptacle can be secured against unintended movement due to pure compression or tensile forces. The sealing member receptacle position with maximum distance to the fluid connection corresponds to a position of the sealing member receptacle in a disconnected state, while the sealing member receptacle position with minimum distance to the fluid connection is preferably present, when a connected state is reached, which is provided for a fluid connection with a mating coupling member. As a precautionary measure, it is noted that the term "sealing member receptacle position" does not refer to a position for receiving the sealing member, but to a position of the sealing member receptacle itself.

The term "threaded" with respect to the coupling element housing threaded portion or hereinafter is not limited to an isometric thread or a thread with oblique threaded flanks, but generally includes a structural formation in which a guiding structure is formed in a helical manner.

Since the coupling member housing threaded portion has a height/length of the thread in the direction of the longitudinal axis which is more than the height/length of the sealing member receptacle guiding structure in this direction, another guiding structure of a member to be connected, such as the mating coupling member guiding structure of a mating coupling member described later, may also be guided in the coupling member housing threaded portion together with the sealing member receptacle guiding structure. The height of the thread is designed in particular in such a way that the sealing member receptacle and the member to be connected are kept at a minimum distance from the fluid connection with a predetermined surface pressure relative to one another during their joint guidance via the coupling member threaded portion until the sealing member receptacle position is reached. Accordingly, the thread height is constant in particular since this also ensures a constant surface pressure over the guiding path. Since the guiding structure of a member to be connected, such as the mating coupling member guiding structure of a mating coupling member, is guided together with the sealing member receptacle guiding structure in the coupling member housing threaded portion for connection, in the following statements on the guidance of the sealing member receptacle guiding structure in the coupling member housing threaded section can be transferred analogously to the joint guidance. Accordingly, for reasons of simplification, the guiding structure of the member to be connected is not explicitly referred to again each time.

The mating coupling member for coupling to the coupling member according to the invention comprises a mating coupling member housing having a mating coupling member fluid connection and a mating coupling side, the mating coupling member housing having a mating coupling member longitudinal axis extending from the mating coupling member fluid connection toward the mating coupling side, and a mating coupling member sealing member, which is arranged in the mating coupling member housing and, together with the mating coupling member housing, forms at least part of a mating coupling side front surface of the mating coupling member, wherein the mating coupling member housing comprises a mating coupling member guiding structure which is configured such that the mating coupling member is guidedly movable relative to the coupling member in the direction of the longitudinal axis by the coupling member housing threaded portion of the coupling member.

The mating coupling member guiding structure may, for example, be formed as at least one projection projecting radially outward with respect to the longitudinal axis. The height of the projection in the direction of the longitudinal axis is in particular less than or equal to the difference between the thread height of the coupling member housing threaded portion in the longitudinal direction and the height of the sealing member receptacle guiding structure in the longitudinal direction, so that it may be guided together with the sealing member receptacle guiding structure in the coupling member housing threaded portion. The height of the mating coupling member guiding structure in the longitudinal direction may be designed to match the surface pressure to be provided between the mating coupling member sealing member and the sealing member of the coupling member.

To increase modularity, however, the mating coupling member guiding structure in the longitudinal direction may also be formed elastically, so that, starting from a relaxed initial state, the mating coupling member guiding structure may be compressed in the longitudinal direction. In the initial state, the height of the mating coupling member guiding structure may thus also be greater than the difference specified previously. The elasticity of the mating coupling member guiding structure may also compensate for deviations from a constant thread height in the longitudinal direction. Also, guided movement in the coupling housing portion may require some force to be applied thereto, so that the risk of an unintended movement, particularly with respect to a preload force applied by the coupling member, is reduced. Alternatively or in addition, however, the mating coupling member guiding structure may also be replaceable, for example as an annular member that may be screwed onto the mating coupling member.

The coupling system according to the invention is configured such that the fluid opening of the coupling member in a connected state with the mating coupling member, in which the sealing member receptacle is in the position with minimum distance to the fluid connection of the coupling member, is arranged at least partially on a side of the mating coupling member sealing member of the mating coupling member facing the mating coupling member fluid connection.

By moving the sealing element receptacle from a position with maximum distance to the fluid connection to a position with minimum distance to the fluid connection and corresponding movement of the mating coupling element through the joint guidance in the coupling housing threaded portion, wherein the mating coupling member sealing member front surface and the coupling member sealing member front surface abut each other in a fluid-tight manner at least in the region of the spike, the mating coupling member sealing member and the mating coupling member sealing member are moved longitudinally along the spike in the direction of the fluid connection. For a fluid connection of the coupling member with the mating coupling member by the spike, the coupling system is configured such that the sealing member and the mating coupling member sealing member are moved together in the direction of the fluid connection of the coupling member to such an extent that the fluid opening of the spike of the coupling system is in a connected state, in which the sealing element receptacle is in the position with minimum distance to the fluid connection of the coupling member, projects at least partially, in particular completely, on a side of the mating coupling sealing member facing away from the mating coupling member front surface into a mating coupling member fluid channel enclosed or formed by the mating coupling member housing. Accordingly, the fluid opening is continuously sealed by the sealing member and the mating coupling sealing member until just before the connected state is reached. When the coupling member and mating coupling member are disconnected, any fluid still on the spike may be wiped off the mating coupling member sealing member, reducing the risk of fluid leakage during or after disconnection.

In addition, the coupling member housing threaded portion of the coupling member is formed such that the mating coupling member guiding structure and the sealing member receptacle guiding structure may be moved together, in particular in a predetermined positional relationship to each other, guided by the coupling member housing threaded portion.

The predetermined positional relationship may, for example, correspond to a position of the coupling member sealing member and the mating coupling member sealing member in which the facing surfaces of the coupling member sealing member and the mating coupling member sealing member abut each other with a predetermined surface pressure. This may be provided, for example, by a constant thread height in conjunction with appropriate dimensioning of the heights of the sealing member receptacle guiding structure and the mating coupling member guiding structure in the longitudinal direction.

In an embodiment of the coupling system, the at least one fluid opening is arranged within the sealing element when the sealing member receptacle with the sealing member is in the position with maximum distance to the fluid connection.

Accordingly, with respect to the foregoing reduction of risk of an unintended movement, leakage of a fluid in a disconnected state may be prevented.

In an embodiment, the sealing member receptacle comprises a sealing member receptacle groove extending from a front surface facing the coupling side in the direction of the longitudinal axis toward the fluid connection and is formed such that a mating coupling member guiding structure portion comprising a mating coupling member guiding structure is at least partially receivable in the sealing member receptacle groove.

The sealing member receptacle groove thus forms a recessed portion in the direction of the fluid connection relative to the coupling side front surface, which serves as a stop. In addition to its function as a stop, the sealing member receptacle groove may also serve as a positioning aid for a member to be connected, such as the mating coupling member. For this purpose, the sealing member receptacle guiding groove may be formed, for example, as an annular outer recessed portion in the radial direction with respect to the longitudinal axis. The inner wall of the coupling member housing may surround this portion in such a way as to form an annular receptacle portion for the member to be connected, which is delimited externally by the coupling member housing or its inner wall, respectively, in the radial direction with respect to the longitudinal axis. When a portion of the member to be connected engages in the sealing member receptacle groove, for example until it reaches the stop formed by the sealing member receptacle groove, this portion covers the part of the sealing member receptacle formed from the stop in the direction of the coupling side. This overlap may further seal the connection of the coupling member with a member to be connected, such as the mating coupling member. In addition, thereby a position of the member to be connected may also be defined in which a guiding structure associated therewith may be inserted into the coupling member housing threaded portion together with the sealing member receptacle guiding structure.

In particular, the coupling member housing threaded portion is formed as a female thread into which the sealing member receptacle guiding structure is receivable.

Thus, the sealing member receptacle guiding structure may be formed in a simple manner. In principle, however, it is also possible to form the coupling member housing threaded portion as a male thread, wherein the sealing member receptacle guiding structure is at least partially formed as a female thread corresponding thereto.

In a further development, the coupling member housing threaded portion comprises at least two separate, in particular at least two opposing, threads.

In conjunction with at least two sealing member receptacle guiding structures correspondingly opposing each other, the sealing member receptacle may be guided in the coupling member housing threaded portion in a more positionally stable manner, since thereby tilting of the sealing member receptacle is prevented. However, the number of threads may also be less than the number of sealing member receptacle guiding structures, for example, in order to insert the sealing member receptacle into the coupling member housing in different orientations and/or to provide for different movements of the sealing member receptacle by means of different threads.

In an embodiment, at least one thread of the coupling member housing threaded portion extends with respect to the longitudinal axis over an angle less than 360°, in particular over an angle of substantially 180°.

The guided movement of the sealing member receptacle may thus take place over a limited angle of rotation, which simplifies handling. In addition, a shortened angle of rotation, i.e. an angle of rotation for reaching a target position that does not comprise several revolutions, facilitates the control of the movement, since several revolutions do not have to be tracked. In this context, optical or haptic marking members may support the movement control.

In an embodiment, at least one thread of the coupling member housing threaded portion has an orthogonal portion with respect to the longitudinal axis at its end facing the fluid connection.

Thus, the inclination of the thread is not continued over this portion. When the sealing member receptacle guiding structure is moved into the orthogonal portion, the sealing member receptacle may not be moved from this position by the application of pure tensile or compressive forces in the direction of the longitudinal axis. Accordingly, the orthogonal portion enables securing of the positioning of the sealing member receptacle in this position, in particular in the position with minimum distance to the fluid connection, when the orthogonal portion corresponds to this position.

In particular, at least one thread of the coupling member housing threaded portion comprises a recessed portion with respect to the longitudinal axis at its end facing the fluid connection, which is recessed with respect to the thread in the direction of the coupling side.

When the sealing member receptacle guiding structure is moved into the recessed portion, the sealing member receptacle may not be moved out of this position by applying pure rotational movements about the longitudinal axis, but must first be moved out of the recessed portion, for example, by applying a compressive force to the sealing member receptacle along the longitudinal axis in the direction of the fluid connection. The positioning of the sealing member receptacle guide structure in the recessed portion preferably corresponds to a position of the sealing member receptacle in the connected state. The recessed portion may be provided alternatively or in addition to the orthogonal portion. In a combination of the recessed portion and orthogonal portion, the recessed portion preferably follows the orthogonal portion in a guiding direction of the sealing member receptacle guiding structure at an end of the thread facing the fluid connection. For example, the sealing member receptacle guiding structure is first moved along the at least one thread having a pitch toward the fluid connection, then reaches the orthogonal portion, and then may be moved into the recessed portion by a continued rotational movement.

In an embodiment, the housing portion is rotatable relative to the longitudinal axis.

The sealing member receptacle may thus be moved along the longitudinal axis via the sealing member receptacle guiding structure by means of a rotational movement of the housing portion about the longitudinal axis. Preferably, the housing portion is a portion rotatably mounted relative to the rest of the housing, so that the rotational movement performed by the housing portion is not transmitted to the rest of the housing. This facilitates handling or connection and disconnection in particular if, for example, further components are already connected to the fluid connection.

Alternatively or in addition, the sealing member receptacle is rotatable relative to the longitudinal axis and/or to the coupling member housing.

Accordingly, the housing portion is not or not only rotated to move the sealing member receptacle via the sealing member receptacle guiding structure in engagement with at least one corresponding thread, but the sealing member receptacle.

According to an embodiment, the sealing member receptacle is supported in the coupling member housing by an elastic member, in particular a compression spring member, which acts in the direction of the longitudinal axis and is arranged between the fluid connection and the sealing member receptacle.

Via the elastic element, the sealing member receptacle may be preloaded in the direction of the coupling side, so that the risk of an unintended movement of the sealing member receptacle in the direction of the fluid connection and thus an unintended release of the fluid opening is further reduced. At the same time, the preload may be used to automatically move the sealing member receptacle from a sealing member receptacle position with minimum distance to the fluid connection back to a sealing member receptacle position with maximum distance to the fluid connection in order to seal the fluid opening again via the sealing member.

The elastic member may be designed as a compression spring, i.e., for example, as a spiral spring, which is arranged between the sealing member receptacle and the fluid connection. Alternatively or in addition, however, the elastic element may also be formed by the sealing member receptacle itself or the sealing member.

In order to be able to retain the sealing member receptacle in the housing on the coupling side despite preloading, the sealing member receptacle guiding portion may already be inserted into the coupling member housing threaded portion in the disconnected state. Alternatively or in addition, the coupling member housing may have a structure that cooperates with the sealing member receptacle accordingly.

According to an embodiment, the mating coupling member housing has at least one mating coupling member guiding structure portion that comprises the mating coupling member guiding structure and is configured to be insertable into a sealing member receptacle groove as described with respect to the coupling member.

The advantages of such a mating coupling member guiding structure portion in cooperation with a sealing member receptacle groove are as described with respect to the sealing member receptacle groove.

The mating coupling member guiding structure portion may, for example, be formed as an end portion facing the mating coupling side, which has at least one radial projection with respect to the portion of the mating coupling member adjoining in the direction of the mating coupling member fluid connection. The height of the radial projection in the longitudinal direction corresponds to or forms the height of the mating coupling member guiding structure. In addition, the radial projection together with the remaining mating coupling member guiding structure portion may form a ring projecting longitudinally beyond the mating coupling member sealing member for engaging the sealing member receptacle groove of the coupling member, which may further seal the connection of the mating coupling member sealing member and the sealing member of the coupling member in the radial direction.

BRIEF DESCRIPTION OF THE DRAWING FIGURES

Features, expediencies and advantages of the invention are also described below with reference to the drawings by way of exemplary embodiments.

Figure 10:
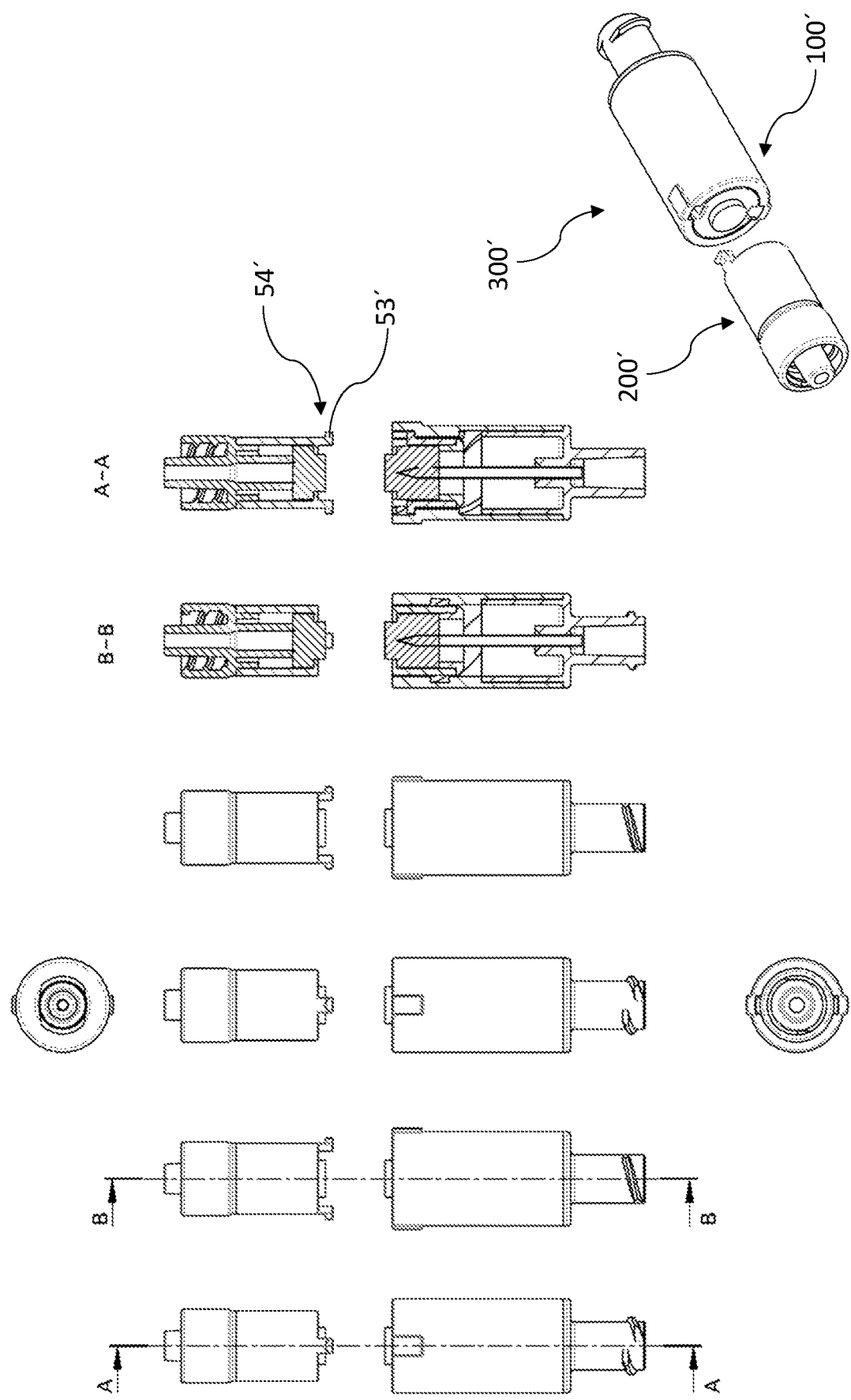
FIG. 10 is an overview of all external views of a coupling system according to a second embodiment, the sectional views along intersection line A-A and intersection line B-B as well as a perspective view in the disconnected state.
Figure 11:
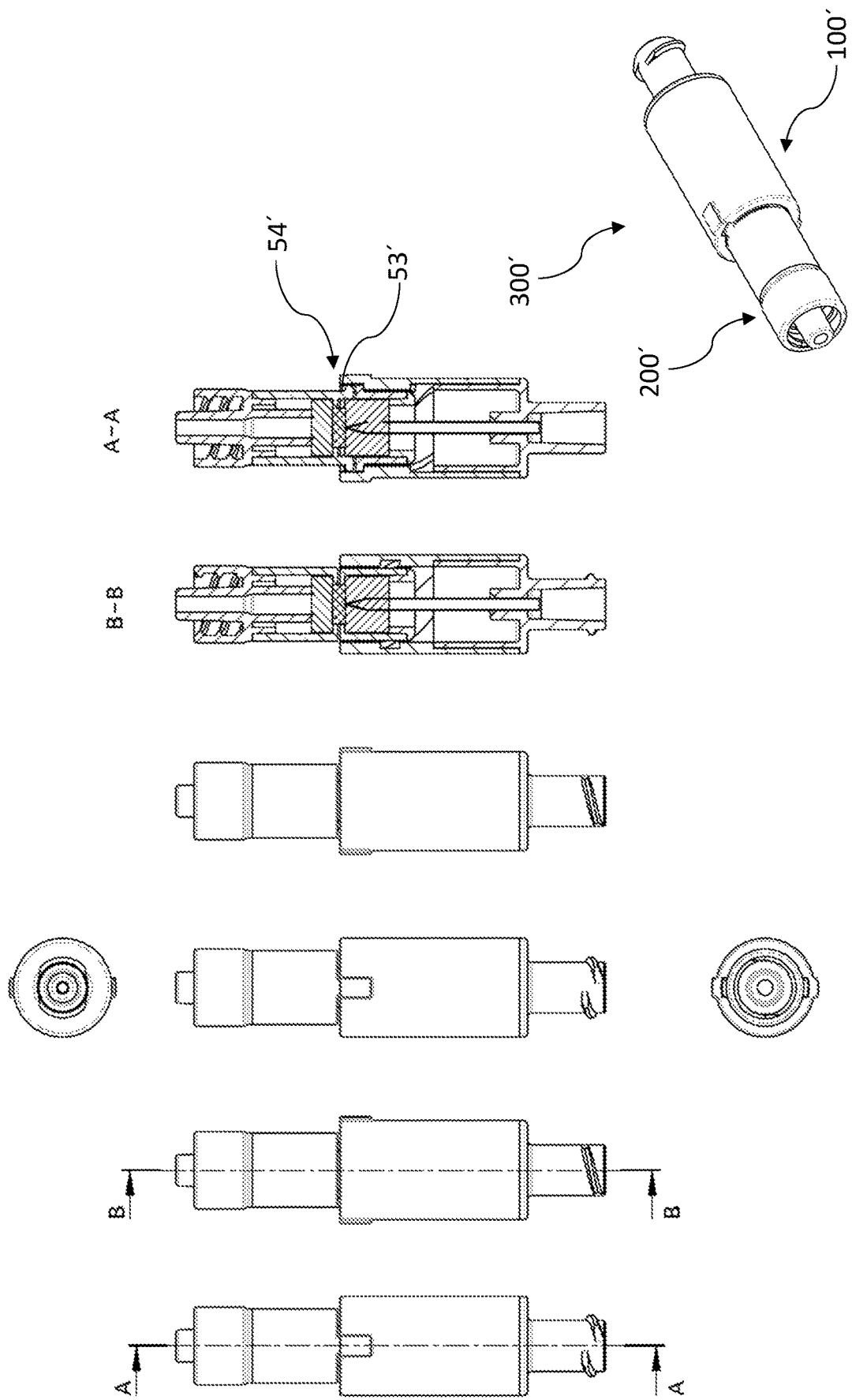
Figure 12:
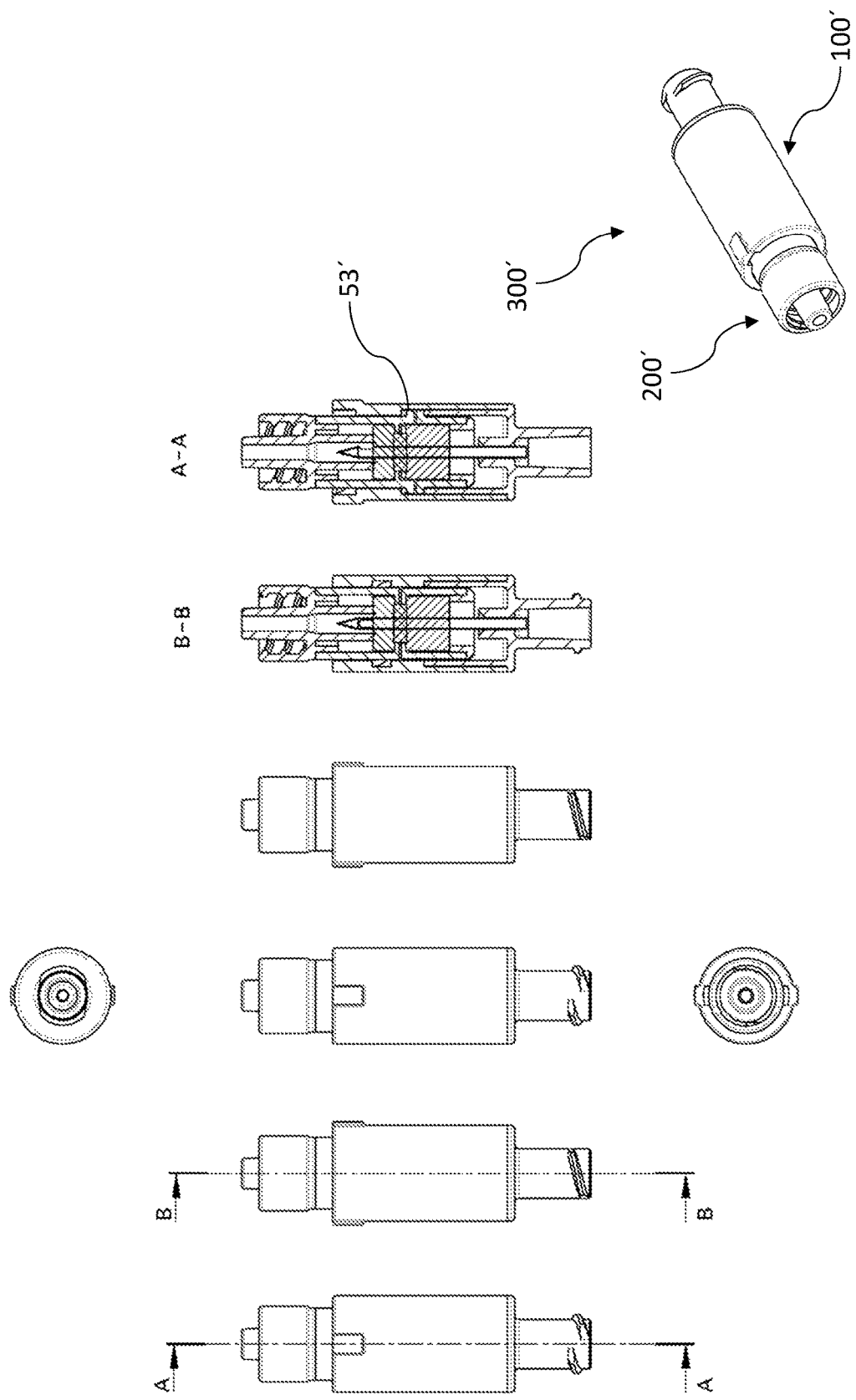

FIG. 11 is an overview of all external views of the coupling system according to FIG. 10, the sectional views along intersection line A-A and intersection line B-B as well as a perspective view in a state in which the mating coupling member has been inserted into the coupling member; and FIG. 12 is an overview of all external views of the coupling system according to FIGS. 10 and 11, the sectional views along intersection line A-A and intersection line B-B, and a perspective view in the connected state.

DETAILED DESCRIPTION

Figure 1:
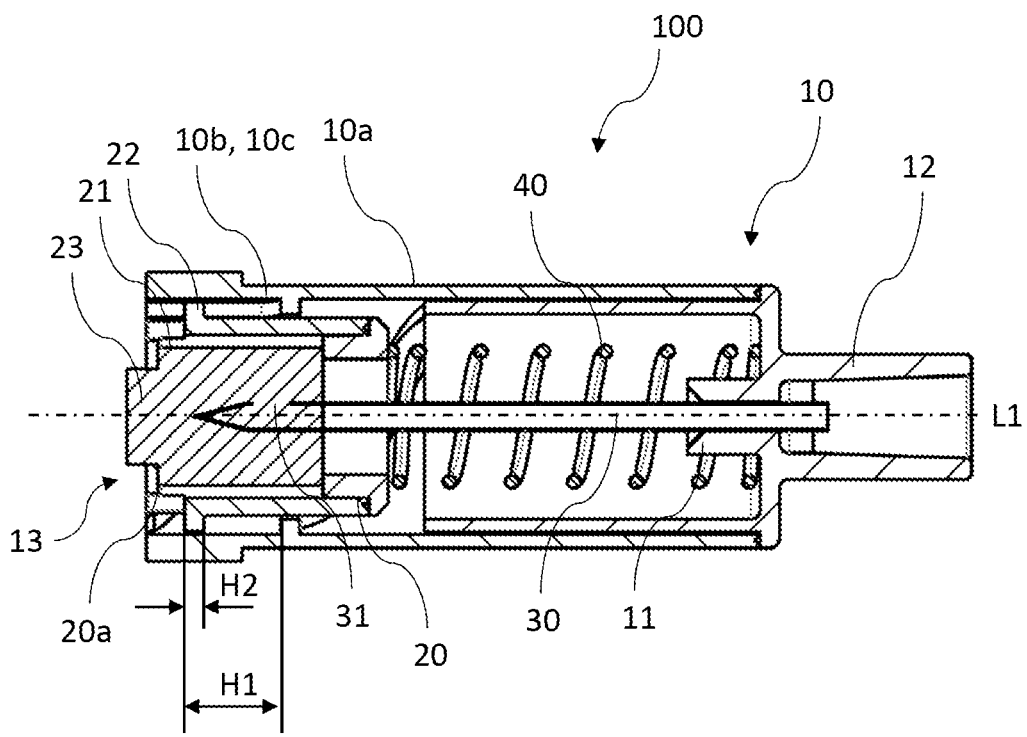
FIG. 1 is a schematic cross-sectional view of a coupling member in a plane parallel to the longitudinal axis of the coupling member housing according to an exemplary first embodiment of the coupling member in a disconnected state.

FIG. 1 shows a cross-sectional view of a coupling member 100 in a plane parallel to the longitudinal axis L1 of a coupling member housing 10 of the coupling member 100 in an exemplary first embodiment. The intersection line A-A corresponds to the intersection line A-A of the coupling system 300 shown in FIG. 6. The longitudinal axis L1 of the coupling member 100 runs from a fluid connection 12 toward a coupling side 13. In addition to the coupling member housing 10, the coupling member 100 comprises a spike receptacle 11, a spike 30 received in the spike receptacle 11, which is formed as fluid channel, a sealing member receptacle 20 having a sealing member receptacle guiding structure 22, a sealing member 23 received in the sealing member receptacle 20, and an elastic member 40, which is arranged between a fluid connection end of the coupling member housing 10 and the sealing member receptacle 20.

The coupling member housing 10 comprises a housing portion 10a, which extends from the connection side portion of the coupling member housing 10 toward the coupling side 13 around the longitudinal axis L1. In the shown embodiment, the housing portion 10a is preferably rotatably supported about the longitudinal axis L1. The housing portion 10a further comprises a coupling member housing threaded portion 10b comprising two threads 10c, wherein, however, also more or less threads 10c may be provided. Here, the threads 10c are each formed as helical grooves extending from the coupling side 13 in the direction of the fluid connection 12 over an angle of 180°. One coupling side end of one thread 10c is opposite a coupling side end of the other thread 10c with respect to the longitudinal axis L1. Accordingly, the respective fluid connection side ends of the threads 10c are also opposed to each other with respect to the longitudinal axis L1.

In the shown disconnected state, the sealing member receptacle 20 is located in a position with maximum distance to the fluid connection 12, and is retained in the coupling member housing 10 by two sealing member receptacle guiding structures 22, each of which engaging one of the threads 10c. The sealing member receptacle guiding structures 22 to be provided primarily serve for the guided movement of the sealing member receptacle 20 along the longitudinal axis L1 of a position of the sealing member receptacle 20 from a position with maximum distance to the fluid connection 12 to a position with minimum distance to the fluid connection 12, and vice versa. Thus, the sealing member 20 may also be retained by other structural designs in the coupling member housing 10, and the respective sealing member receptacle guiding structures 22 only fully engage the respective threads 10c by moving the sealing member receptacle 20 along the longitudinal axis L1 toward the fluid connection 12.

As apparent from FIG. 1, the thread 10c in the direction of the longitudinal axis L1 is larger than the length of the sealing member receptacle guiding structure 22 in this direction, i.e. the height/length H1 of the thread 10c in the direction of the longitudinal axis L1 is larger than the height/length H2 of the sealing member receptacle guiding structure in this direction. Here, the height/length H1 of the thread is constant, to be capable of maintaining a surface pressure between the facing surfaces of the sealing member 23 and a mating coupling member sealing member 60 to be described later constant over the guiding path. The sealing member receptacle guiding structure is thus movable in the thread 10c in the direction of the longitudinal axis L1. The extension of the thread 10c in the direction of the longitudinal axis in conjunction with the extension of the sealing member receptacle guiding structure in this direction should be thereby selected such that the sealing member 23 still seals the fluid opening 31 of the spike 30, even if the sealing member receptacle guiding structure rests against the boundary of the thread 10c facing the fluid connection 12. The sealing member 23 is accordingly arranged in the sealing member receptacle 20 and dimensioned such that it fully surrounds, i.e. seals, a fluid opening 31, which is arranged in an end portion of the spike 30 facing the coupling side 13, in a disconnected state.

The coupling member 100 further comprises an elastic member 40, which is here formed by a compression spring. The elastic member 40 is arranged in the coupling member housing 10 and is supported against a fluid connection side housing portion and the sealing member receptacle 20. Hereby, the sealing member receptacle 20 is preloaded toward the coupling side 13 such that it abuts with the sealing member receptacle structure 22 on the side of the thread 10c facing away from the fluid connection 12 without further application of force and is retained in this position under preload.

The sealing member receptacle 20 further comprises a sealing member receptacle groove 21, which is recessed in the direction of the longitudinal axis L1 from the front surface 20a toward the fluid connection 12. The sealing member receptacle groove 22 extends annular around the longitudinal axis L1 and is delimited by the inner wall of the coupling member housing 10 in the radial direction.

The movement of the sealing member receptacle 20 from a position with maximum distance to the fluid connection 12 toward a position with minimum distance to the fluid connection 12, or vice versa, takes place by the guidance of the respective sealing member receptacle guiding structures 22 in the respective threads 10c toward the fluid connection 12 and away therefrom depending on the direction of movement to be provided. For this purpose, the housing portion 10a and/or the sealing member receptacle 20 may be intentionally set into a rotational movement. This corresponds to an intentional screwing in or out. Alternatively or in addition, however, the application of a compression or tensile force depending on the direction of movement to be provided may be sufficient, if the housing portion 10a and/or the sealing member receptacle 20 are rotatably supported such that hereby the housing portion 10a and/or the sealing member receptacle 20 screw in or out autonomously.

At this point, it is further noted that the movement of the sealing member receptacle 20 from a position with maximum distance to the fluid connection 12 toward a position with minimum distance to the fluid connection 12, or vice versa, is provided for a connection with a mating coupling member, as the mating coupling member 200 or 200' as described later, in accordance with the application. According to the previous and following explanations, such a mating coupling member has a mating coupling member guiding structure, such as the mating coupling member guiding structure 53, which is guided together with the sealing member receptacle guiding structure 22 in the thread 10c for connection. Accordingly, explanations regarding the guiding of the sealing member guiding structure 22 are equally applicable to the joint guiding of the sealing member guiding structure 22 and a mating coupling member guiding structure.

Figure 2:
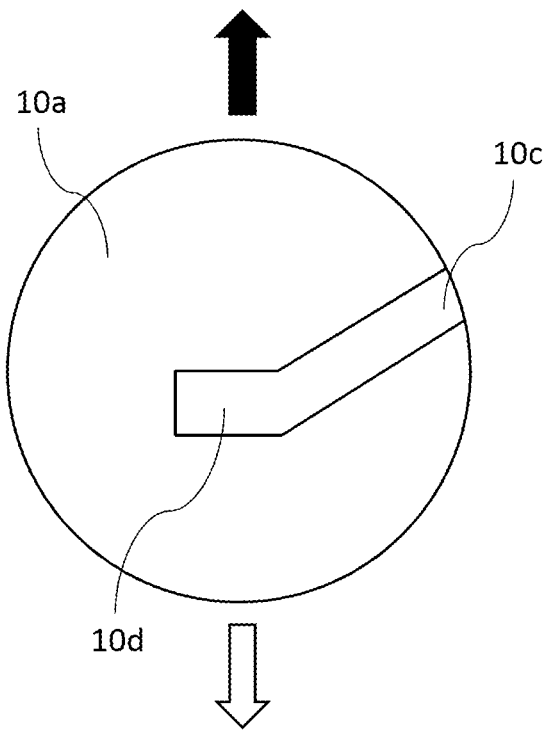
FIG. 2 is a section of an exemplary end of a fluid connection side thread with an orthogonal portion in a top view in a viewing direction on the longitudinal axis.
Figure 3:
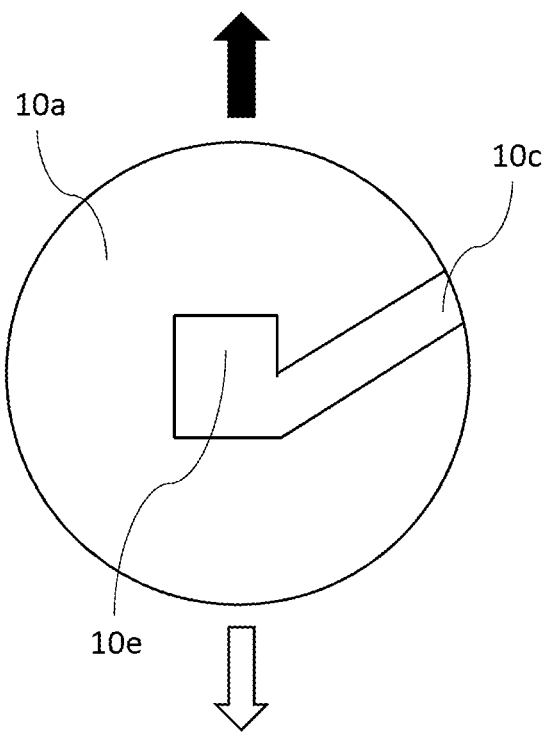
FIG. 3 is a section of another exemplary end of a fluid connection side thread with a recessed portion in a top view in a viewing direction on the longitudinal axis.

Insofar as autonomous screwing or unscrewing is possible in principle, or for other securing considerations, it may be advantageous to secure a position of the respective sealing member receptacle guiding structures 22 in the respective threads 10c in a position corresponding to a position with minimum distance to the fluid connection 12 against an unintentional change of position. Possible exemplary embodiments for such position lock are shown in FIGS. 2 and 3, each of which shows a section of one end of a thread 10c on the fluid connection side in a top view in the direction of view on the longitudinal axis L1. The filled arrow represents in each case a longitudinal axis direction in the direction of the coupling side 13, while the non-filled arrow represents a longitudinal axis direction in the direction of the fluid connection 12.

FIG. 2 illustrates an exemplary end of a fluid connection side thread 10c with an orthogonal portion 10d with respect to the longitudinal axis L1. When a sealing member receptacle guiding structure 22 is moved into the orthogonal portion 10d, an applied compressive or tensile force does not cause rotational movement of the housing portion 10a and/or the sealing member receptacle 20. Accordingly, the risk of an unintended movement is reduced.

Alternatively, FIG. 3 shows an exemplary end of a fluid connection side thread 10c with a recessed portion 10e in the direction of the filled arrow. When a sealing member receptacle guiding structure 22 is moved into the recessed portion 10e, the position of the sealing member receptacle 20 is secured thereby against rotational movement. This position of the sealing member receptacle guiding structure 22 corresponds to a position of the sealing member receptacle 20 in a connected state, in which the sealing member receptacle 20 is in the position with minimum distance to the fluid connection 12 of the coupling member 100. Strictly speaking, the position of the sealing member receptacle 20 with minimum distance to the fluid connection 12 is formed by the position of the transition between the portion of the thread 10c still having a pitch and the recessed portion 10e. However, since the back offset is insignificant at the application scale, the position of the sealing member receptacle 20 when the sealing member guide structure 22 engages the recessed portion 10e is also understood to be the position with minimum distance to the fluid connection 12.

To release the position lock via the recessed portion 10e, the sealing member receptacle guiding structure 22 must first be relatively moved again in the direction of the fluid connection 12 in order to be able to overcome the recessed portion 10e. This type of position assurance is further supported via the provision of the elastic member 40. However, the position lock according to FIG. 3 does not preclude a position lock according to FIG. 2, so that combined position locks may also be applicable.

Figure 4:
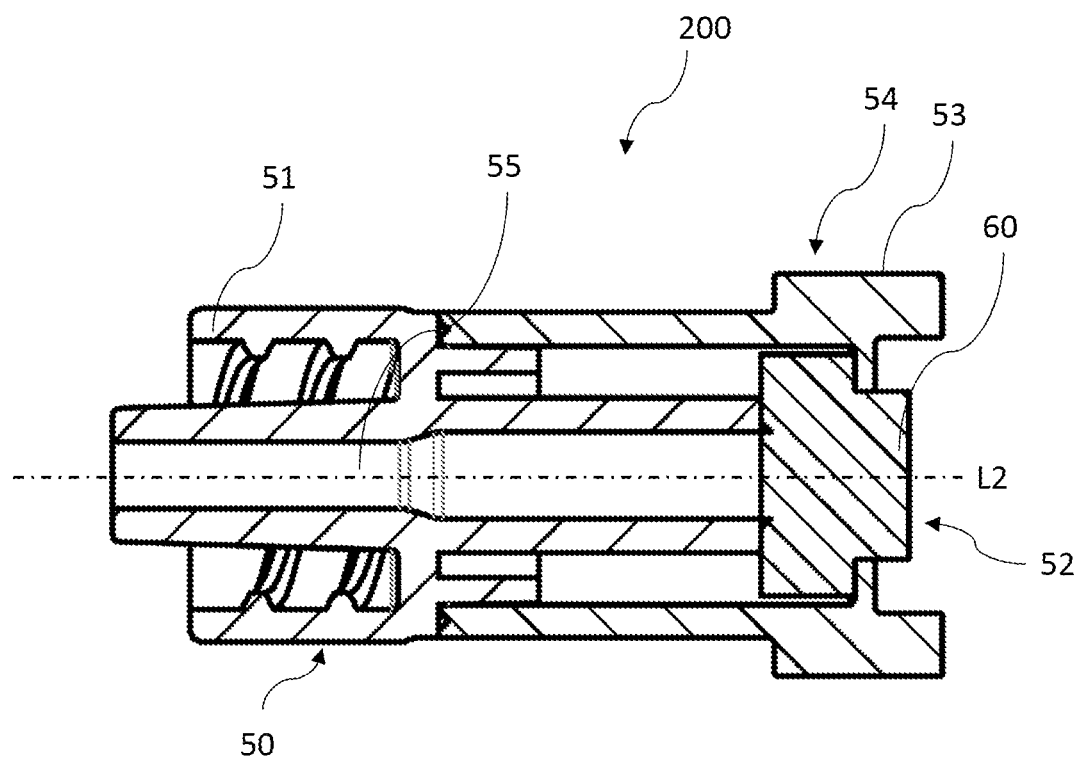
FIG. 4 is a schematic cross-sectional view of a mating coupling member in a plane parallel to the mating coupling member longitudinal axis of the mating coupling member housing according to an exemplary first embodiment of the mating coupling member in the disconnected state.

FIG. 4 shows a schematic cross-sectional view of a mating coupling member 200 in a plane parallel to a mating coupling member longitudinal axis L2 of a mating coupling member housing 50, according to an exemplary first embodiment of the mating coupling member 200 in the disconnected state. The mating coupling member 200 comprises the mating coupling member housing 50 having a mating coupling member fluid connection 51 and a mating coupling side 52, wherein the mating coupling member housing 50 has the mating coupling member longitudinal axis L2 extending from the mating coupling member fluid connection 51 toward the mating coupling side 52. In addition, the mating coupling member comprises a sealing member 60 arranged at an end of the mating coupling member 200 facing the mating coupling side 52 in the mating coupling member housing 50 and forming, together with the mating coupling member housing 50, a mating coupling side front surface of the mating coupling member 200. The mating coupling member sealing member 60 seals on the mating coupling side a mating coupling member fluid connection 55 extending from the mating coupling member fluid connection 51 toward the mating coupling side 52, the mating coupling member fluid connection 55 extending coaxially with the mating coupling member longitudinal axis L2 in this example.

Further, the mating coupling member housing 50 has a mating coupling member guiding structure portion 54 formed by an end portion of the mating coupling member housing 50 on the coupling side 52. The mating coupling member guiding structure portion 54 includes two mating coupling member guiding structures 53 formed as two projections extending radially outward with respect to the longitudinal axis L2. The mating coupling member guiding structures 53 are provided to engage with and be guided in a coupling member housing threaded portion, such as the coupling member housing threaded portion 10b. Moreover, the mating coupling member guiding structures 53 together with the remaining mating coupling member guiding structure portion 54 form a ring projecting in the direction of the longitudinal axis L2 beyond the mating coupling member sealing member 60 for engagement with a sealing member receptacle groove, such as the sealing member receptacle groove 21 of the coupling member 100, which may further seal the connection of the mating coupling member sealing member 200 and the sealing member of the coupling member in the radial direction.

Figure 5:
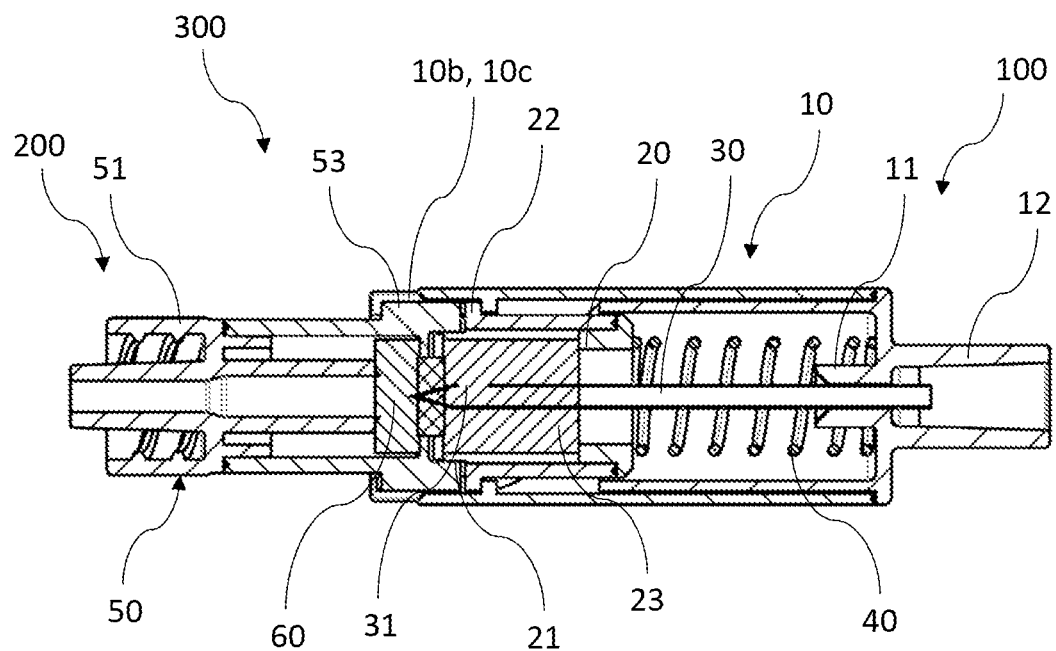
FIG. 5 is a schematic cross-sectional view of a coupling system with a coupling member according to FIG. 1 and a mating coupling member according to FIG. 4 in a plane parallel to the longitudinal axis in a state in which the mating coupling member has been inserted into the coupling member.
Figure 6:
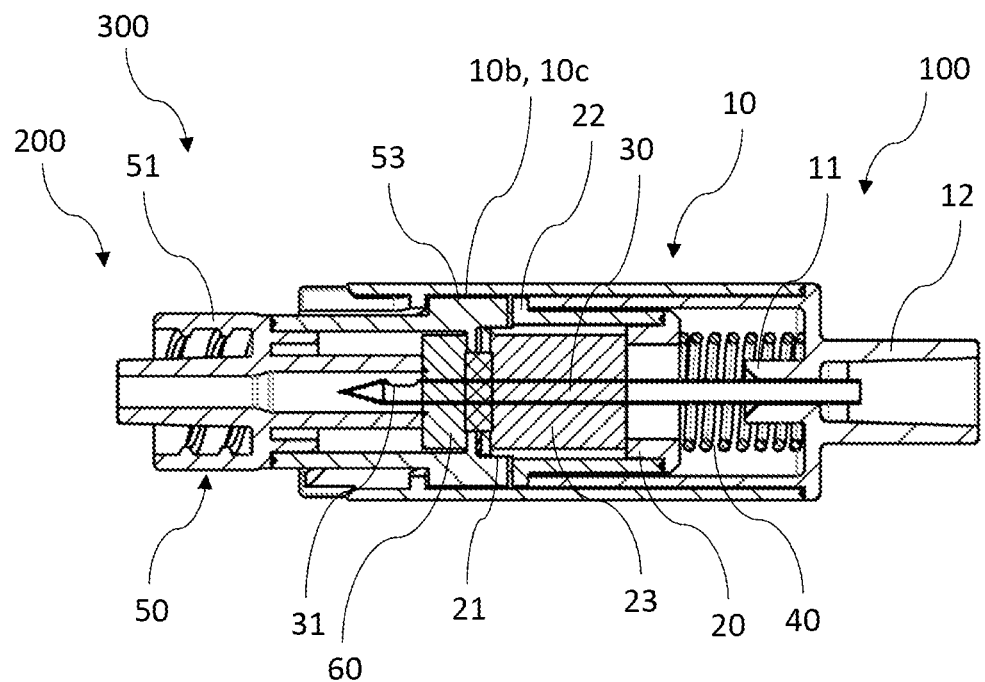
FIG. 6 is a schematic cross-sectional view of a coupling system according to FIG. 5 in a plane parallel to the longitudinal axis in the connected state.

With reference to FIGS. 5 and 6, the interaction of the coupling member 100 with a mating coupling member 200 in a coupling system 300 is described below by way of example.

For this purpose, FIG. 5 shows a schematic cross-sectional view of a coupling system 300 with a coupling member 100 according to FIG. 1 and a mating coupling member 200 according to FIG. 4 in a plane parallel to the longitudinal axis L1 or mating coupling member longitudinal axis L2 in a state, in which the mating coupling member has been inserted into the coupling member. For reasons of simplicity, the respective longitudinal axes L1 or L2 are not drawn in here. For this purpose, reference is made to FIGS. 1 and 4.

By inserting the mating coupling member 200 into the coupling member 100, the sealing member receptacle 20 according to FIG. 5 is initially moved from its disconnected state with a sealing member receptacle position with maximum distance to the fluid connection 12 to a position, in which the sealing member receptacle guiding structures 22 abuts against the boundary of the thread 10c facing the fluid connection 12. This corresponds to a position of the mating coupling member 200, at which the mating coupling member receptacle guiding structures 53 abut the sealing member receptacle guiding structures 22 and may be moved together therewith into the thread 10c. Joint guidance of the mating coupling member receptacle guiding structures 53 and the sealing member receptacle guiding structures 22 in the thread 10c is accomplished by relative rotation between the mating coupling member 200 and the coupling member 100 in accordance with a screwing or unscrewing operation. Alternatively or in addition, however, the application of a compressive or tensile force in dependence on the direction of movement to be provided may be sufficient if the housing portion 10a and/or the sealing member receptacle 20 are rotatably mounted in such a manner that the housing portion 10a and/or the sealing member receptacle 20 thereby autonomously screws in or unscrews. As a result of the form fit between the mating coupling member receptacle guiding structures 53 and the sealing member receptacle guiding structures 22 in conjunction with the thread 10c, the facing surfaces of the mating coupling member receptacle guiding structure 60 and the sealing member receptacle guiding structure 23 are guided in positionally fixed relationship to each other along the thread 10c. The positionally fixed relationship may correspond to a minimum surface pressure, which may be further supported by the spring force of the elastic member 40.

By moving the mating coupling member 200 in the coupling member 100 in the direction of the fluid connection 12, a connected state may then be achieved, which is intended for fluid connection of the mating coupling member 200 and coupling member 100 for fluid exchange.

For this purpose, FIG. 6 shows a schematic cross-sectional view of a coupling system 300 according to FIG. 5 in a plane parallel to the longitudinal axis L1 or mating coupling element longitudinal axis L2 in the connected state. Again, for simplicity, the respective longitudinal axes L1 and L2 are not drawn and reference is again made accordingly to FIGS. 1 and 4.

The movement of the mating coupling member 200 in the coupling member 100 in the direction of the fluid connection 12 up to the fluid connection side end of the threads 10c, and thus the movement of the sealing member receptacle 20 up to the fluid connection side end of the threads 10c, is carried out here, for example, by rotation of the mating coupling member 200 or also by the mating coupling member 200 and the coupling member 100 moving towards one another when the housing portion 10a and/or the sealing member receptacle 20 are rotatably mounted in such a manner as described above. Thus, when the mating coupling member receptacle guiding structures 53 and the sealing member receptacle guiding structures 22 have reached the fluid connection side end of the threads 10c, the sealing member receptacle 20 is in a sealing member receptacle position with minimum distance to the fluid connection 12. This position corresponds to a connected state in which the fluid opening 31 protrudes into the fluid passage 60 via the side of the mating coupling member sealing member 60 facing the mating coupling member fluid connection 51, thus forming a fluid connection.

Figure 7:
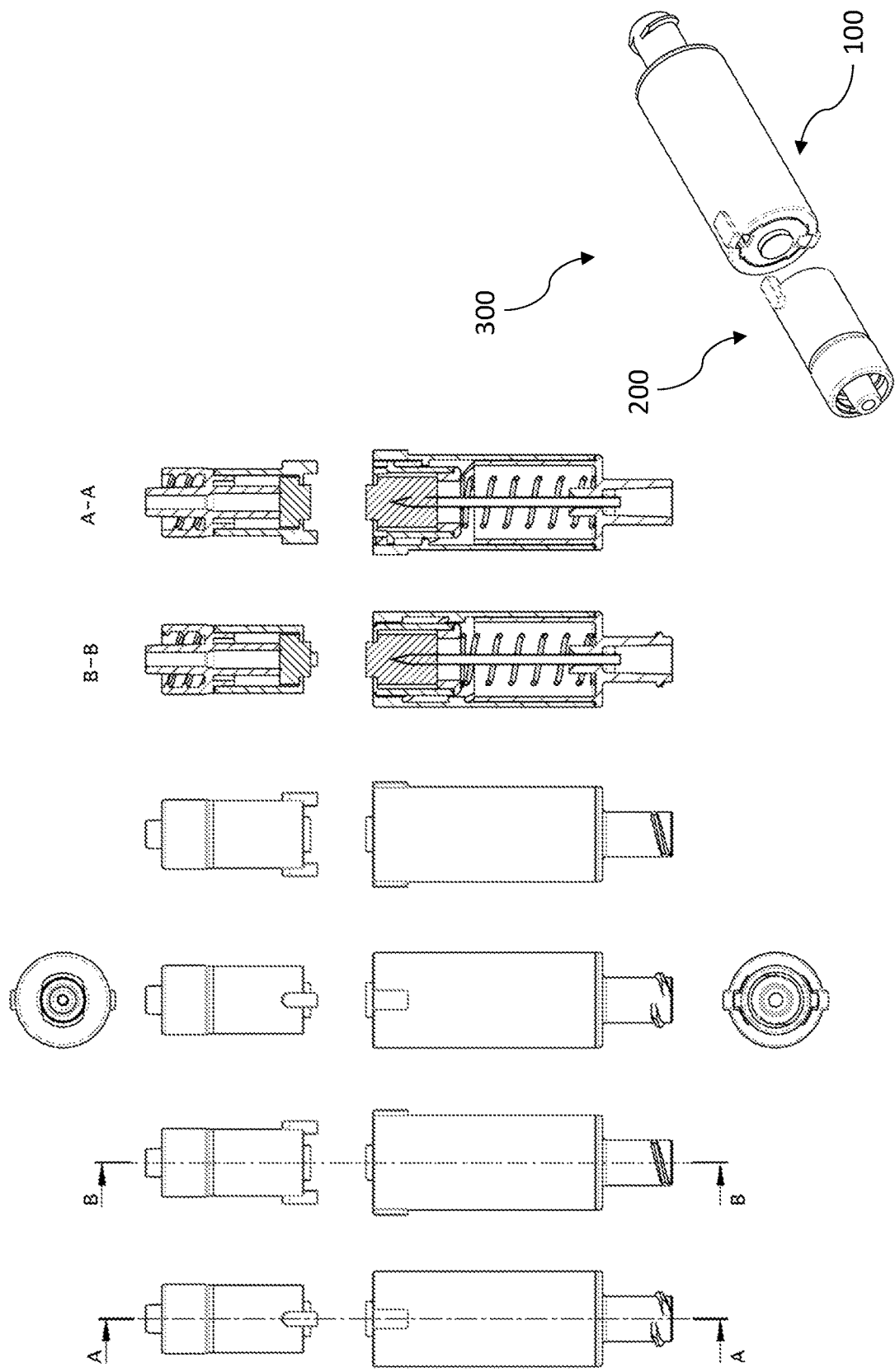
FIG. 7 is an overview of all external views of the coupling system according to FIGS. 4 and 5, the sectional views along intersection line A-A and intersection line B-B, and a perspective view in the disconnected state.
Figure 8:
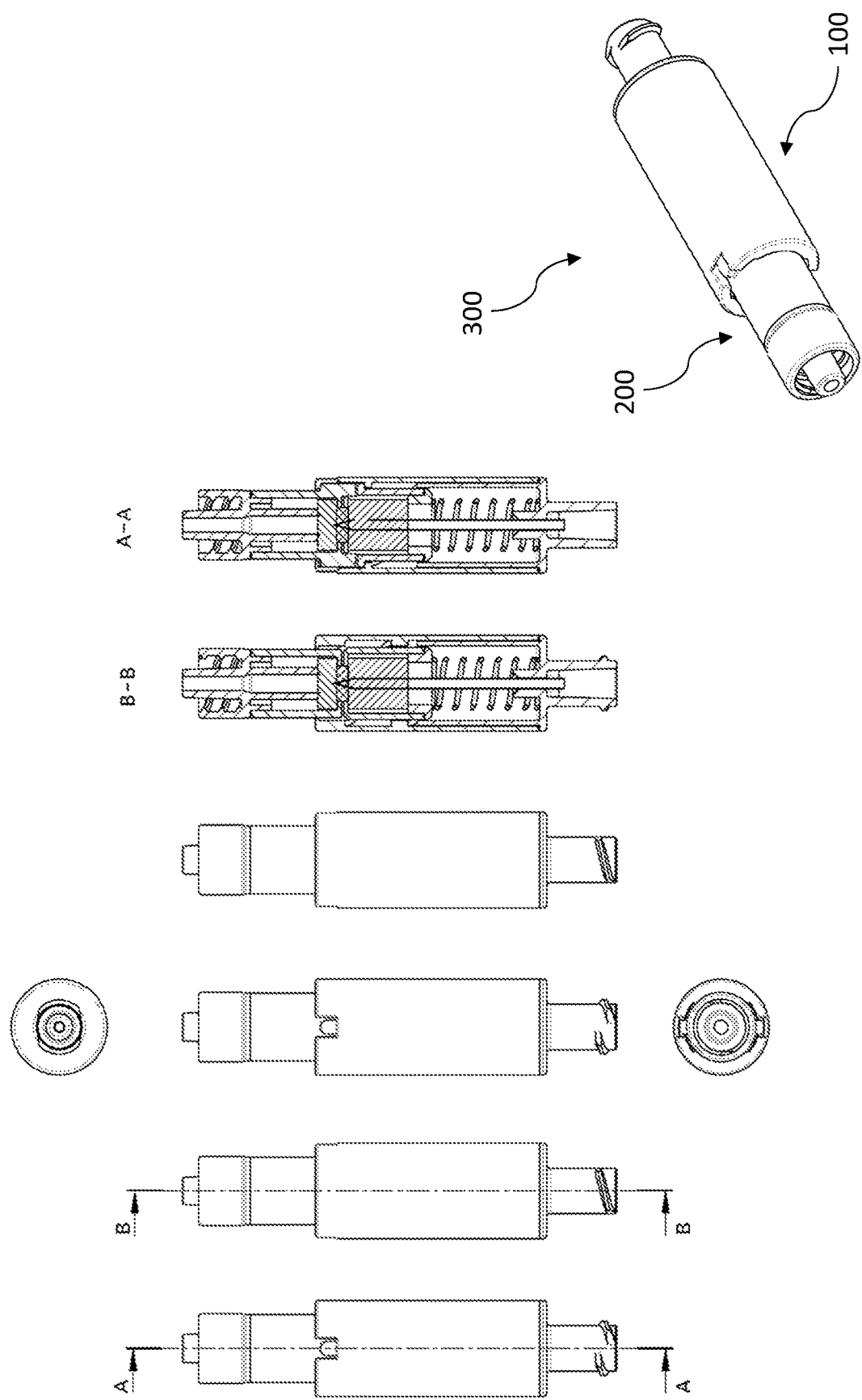
FIG. 8 is an overview of all external views of the coupling system according to FIG. 7 or FIGS. 4 and 5, the sectional views along intersection line A-A and intersection line B-B, and a perspective view in a state in which the mating coupling member has been inserted into the coupling member.
Figure 9:
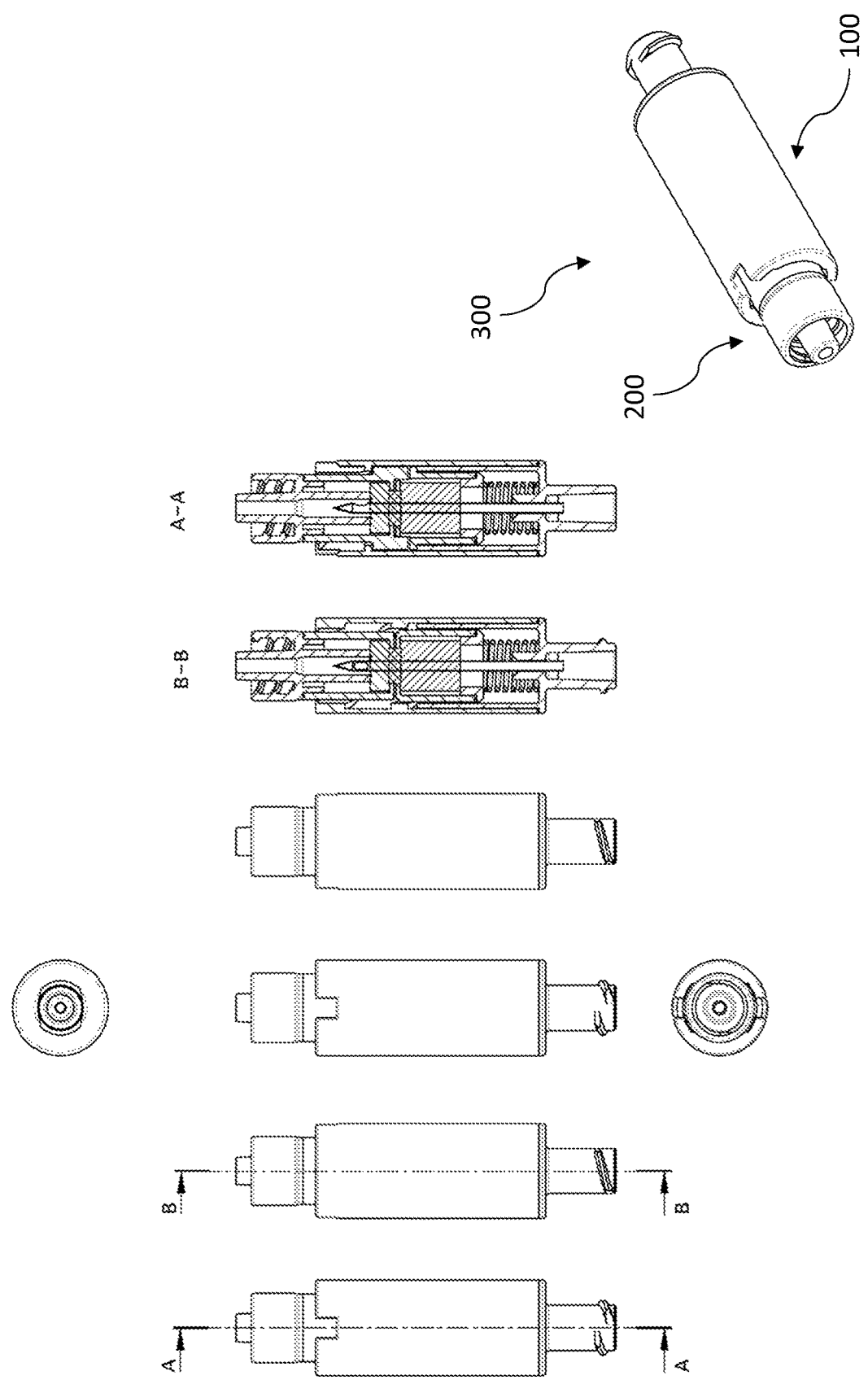
FIG. 9 is an overview of all external views of the coupling system according to FIGS. 7 and 8 or FIGS. 4 and 5, the sectional views along intersection line A-A and intersection line B-B, and a perspective view in the connected state.

FIG. 7 shows complementarily an overview of all external views of the coupling system 300 according to FIGS. 4 and 5, the sectional views along the intersection line A-A and intersection line B-B, as well as a perspective view in the disconnected state. This reveals further design features of the embodiment described. Similarly, FIG. 8 shows an overview of the coupling system 300 according to FIG. 7 in a state in which the mating coupling member has been inserted into the coupling member and FIG. 9 in a connected state.

FIGS. 10 to 12 show corresponding overviews of a coupling system 300' according to a second embodiment in a disconnected state (FIG. 10), a state in which the mating coupling member has been inserted into the coupling member (FIG. 11) and a connected state (FIG. 12).

The coupling system 300' according to the second embodiment comprises a coupling member 100' and a mating coupling member 200'. The coupling system 300' of the second embodiment differs primarily from the coupling system 300 of the first embodiment by the mating coupling member 200' and the corresponding design of the coupling member 100'.

The mating coupling member 200' comprises a mating coupling member guiding structure portion 54' having two mating coupling member guiding structures 53' which are shortened in the direction of the longitudinal axis L2 compared to the mating coupling member guiding structures 53 of the first embodiment. The thread 10c of the coupling member 100' is thus also shorter in the direction of the longitudinal axis L1 than that of the coupling member 100. By shortening the mating coupling member guiding structures 53', for example, the start of the thread 10c in the coupling member 100' may be moved further back in the direction of the fluid connection 12. Guided movement of the mating coupling member guiding structures 53', and thus movement of the sealing member receptacle 20 of the coupling member 100 which then exposes the fluid opening 31 of the spike 30, may thus be delayed until the sealing member receptacle 20 is securely radially sealed by the mating coupling member guiding structure portion 54. Appropriate securing may alternatively or in addition also be achieved by the mating coupling member guiding structures 53 or 53' not being provided directly at the end of the mating coupling member guiding structure portion 54 or 54' facing the mating coupling side 52, but only beginning to be recessed therefrom in the direction of the mating coupling member fluid connection 51.

The invention is not limited to the described embodiments. In particular, certain features of an embodiment are in principle applicable to other embodiments, unless reasonably precluded.

The invention claimed is:

1. A coupling system for a closed fluid transfer system, the coupling system comprising:
A) a coupling member comprising:
a coupling member housing comprising a fluid connection and a coupling side, wherein the coupling member housing provides a longitudinal axis extending from the fluid connection toward the coupling side;
a spike with at least one fluid opening, which is held in a spike receptacle of the housing arranged at the fluid connection and extends into the coupling member housing in the direction of the longitudinal axis, wherein the at least one fluid opening is arranged in an end portion of the spike facing the coupling side;
a sealing member receptacle arranged in the coupling member housing on the coupling side; and
a sealing member arranged in the sealing member receptacle,
wherein the coupling member housing comprises a housing portion, which at least partially surrounds the sealing member receptacle in an axial direction with respect to the longitudinal axis and comprises a coupling member housing threaded portion on the inner surface facing the sealing member;
wherein the sealing member receptacle with the sealing member is moveable in the direction of the longitudinal axis between a sealing member receptacle position with maximum distance to the fluid connection and a sealing member receptacle position with minimum distance to the fluid connection, and wherein the coupling member housing threaded portion is configured such that a sealing member receptacle guiding structure of the sealing member receptacle is movable in engagement with the coupling member housing threaded portion between the sealing member receptacle position with maximum distance to the fluid connection and the sealing member receptacle position with minimum distance to the fluid connection, wherein the coupling member housing threaded portion provides a height/length of the thread in the direction of the longitudinal axis between the sealing member receptacle position with maximum distance to the fluid connection and the sealing member receptacle position with minimum distance to the fluid connection, which is more than the height/length of the sealing member receptacle guiding structure in this direction; and B) a mating coupling member for coupling with the coupling member, the mating coupling member comprising:

a mating coupling member housing comprising a mating coupling member fluid connection and a mating coupling side, wherein the mating coupling member housing comprises a mating coupling member longitudinal axis extending from the mating coupling member fluid connection toward the mating coupling side, and a mating coupling member sealing member, which is arranged in the mating coupling member housing and forms at least a part of a mating coupling side front surface of the mating coupling element together with the mating coupling member housing, wherein the mating coupling member housing comprises a mating coupling member guiding structure, which is configured such that the mating coupling member is movably guided in the direction of the longitudinal axis relative to the coupling member by the coupling member housing threaded portion of the coupling member, wherein the coupling system is configured such that the fluid opening of the coupling member in a state connected to the mating coupling member, in which the sealing member receptacle is located in the position with minimum distance to the fluid connection of the coupling member, is at least partially arranged on a side of the mating coupling member sealing member of the mating coupling member facing toward the mating coupling member fluid connection, and wherein the coupling member housing threaded portion of the coupling member is configured such that the mating coupling member guiding structure and the sealing member receptacle structure are jointly movable guided by the coupling member housing threaded portion.

2. The coupling system according to claim 1, wherein the at least one fluid opening is arranged within the sealing member, when the sealing member receptacle with the sealing member is located in the position with maximum distance to the fluid connection.

3. The coupling system according to claim 1, wherein the sealing member receptacle comprises a sealing member receptacle groove, which extends from a front surface facing the coupling side in the direction of the longitudinal axis toward the fluid connection and is configured such that a mating coupling member guiding structure portion comprising a mating coupling member guiding structure is at least partially receivable in the sealing member receptacle groove.

4. The coupling system according to claim 1, wherein the coupling member housing threaded portion is formed as female thread, in which the sealing member receptacle guiding structure is receivable.

5. The coupling system according to claim 1, wherein the coupling member housing threaded portion comprises at least two separate threads.

6. The coupling system according to claim 5, wherein the at least two separate threads are opposed to each other.

7. The coupling system according to claim 1, wherein at least one thread of the coupling member housing thread portion extends over an angle of less than 360° with respect to the longitudinal axis.

8. The coupling system according to claim 7, wherein at least one thread of the coupling member housing thread portion extends over an angle of substantially 180° with respect to the longitudinal axis.

9. The coupling system according to claim 1, wherein at least one thread of the coupling member housing thread portion comprises an orthogonal portion with respect to the longitudinal axis at its end facing the fluid connection.

10. The coupling system according to claim 1, wherein at least one thread of the coupling member housing thread portion comprises a recessed portion relative to the longitudinal axis at its end facing the fluid connection, which is recessed in the direction of the coupling side with respect to the thread.

11. The coupling system according to claim 1, wherein the housing portion is rotatable relative to the longitudinal axis.

12. The coupling system according to claim 1, wherein the sealing member receptacle is rotatable relative to the longitudinal axis and/or the coupling member housing.

13. The coupling system according to claim 1, wherein the sealing member receptacle supported in the coupling member housing by an elastic member.

14. The coupling system according to claim 13, wherein the elastic member is a compression spring member, which acts in the direction of the longitudinal axis and which is arranged between the fluid connection and the sealing member receptacle.

15. The coupling system according to claim 1, wherein the mating coupling member housing comprises at least one mating coupling member guiding structure portion, which comprises the mating coupling member guiding structure and which is configured such that it is insertable in a sealing member receptacle groove comprised by the sealing member receptacle, which extends from a front surface facing the coupling side in the direction of the longitudinal axis toward the fluid connection and is configured such that a mating coupling member guiding structure portion comprising the mating coupling member guiding structure is at least partially receivable in the sealing member receptacle groove.

16. The coupling system according to claim 1, wherein the coupling member housing threaded portion of the coupling member is configured such that the mating coupling member guiding structure and the sealing member receptacle structure are jointly movable guided in a predetermined positional relationship to each other by the coupling member housing threaded portion.

* * * * *